US011235074B2

(12) United States Patent
Lascola

(10) Patent No.: US 11,235,074 B2
(45) Date of Patent: *Feb. 1, 2022

(54) CONTRAST AGENTS FOR MAGNETIC RESONANCE IMAGING

(71) Applicant: Duke University, Durham, NC (US)

(72) Inventor: Christopher David Lascola, Durham, NC (US)

(73) Assignee: Duke University, Durham, NC (US)

(*) Notice: Subject to any disclaimer, the term of this patent is extended or adjusted under 35 U.S.C. 154(b) by 54 days.

This patent is subject to a terminal disclaimer.

(21) Appl. No.: 16/946,056

(22) Filed: Jun. 4, 2020

(65) Prior Publication Data
US 2020/0297873 A1 Sep. 24, 2020

Related U.S. Application Data

(63) Continuation of application No. 15/812,013, filed on Nov. 14, 2017, now Pat. No. 10,695,447, which is a continuation of application No. 15/461,628, filed on Mar. 17, 2017, now Pat. No. 10,111,970, which is a continuation of application No. PCT/US2016/054478, filed on Sep. 29, 2016.

(60) Provisional application No. 62/234,986, filed on Sep. 30, 2015, provisional application No. 62/291,138, filed on Feb. 4, 2016.

(51) Int. Cl.
| A61K 49/06 | (2006.01) |
| A61K 49/10 | (2006.01) |
| A61B 5/00 | (2006.01) |
| A61K 9/00 | (2006.01) |
| A61B 5/055 | (2006.01) |
| A61K 9/08 | (2006.01) |
| A61K 47/02 | (2006.01) |
| A61K 47/26 | (2006.01) |

(52) U.S. Cl.
CPC ............ A61K 49/06 (2013.01); A61B 5/0042 (2013.01); A61B 5/0044 (2013.01); A61B 5/055 (2013.01); A61K 9/0019 (2013.01); A61K 9/08 (2013.01); A61K 47/02 (2013.01); A61K 47/26 (2013.01); A61K 49/10 (2013.01)

(58) Field of Classification Search
CPC .......... A61K 49/00; A61K 51/04; A61K 9/00; A61K 5/00; A61K 5/04
See application file for complete search history.

(56) References Cited

U.S. PATENT DOCUMENTS

| 4,639,364 A | 1/1987 | Hoey | |
| 5,260,050 A | 11/1993 | Ranney | |
| 5,264,661 A | 11/1993 | Luettgen | B60R 16/0239 174/539 |
| 5,624,661 A * | 4/1997 | Unger | A61K 49/08 424/9.35 |
| 5,985,245 A * | 11/1999 | Golman | A61K 49/18 424/9.3 |
| 6,278,893 B1 | 8/2001 | Ardenkj-Larson et al. | |
| 7,060,731 B2 * | 6/2006 | Juelsrud | A61P 37/06 514/668 |
| 9,655,983 B2 | 5/2017 | Meyer et al. | |
| 2009/0297441 A1 | 12/2009 | Canham | A61K 51/1244 424/1.61 |
| 2011/0008252 A9 | 1/2011 | Hjelstuen et al. | |
| 2014/0154185 A1 | 6/2014 | Van Zijl et al. | |
| 2014/0234210 A1 | 8/2014 | Lin et al. | |
| 2014/0350193 A1 | 11/2014 | Axelsson et al. | |
| 2017/0189561 A1 | 7/2017 | Lascola | |

FOREIGN PATENT DOCUMENTS

| CN | 102579329 | 7/2012 |
| CN | 102579329 A | 7/2012 |
| CN | 102757922 | 10/2012 |
| CN | 102757922 A | 10/2012 |
| EP | 0123314 | 10/1984 |
| JP | 06-181890 | 7/1994 |
| JP | H09227414 | 9/1997 |
| JP | 2011-145297 | 7/2011 |
| WO | 1997/30736 | 8/1997 |
| WO | 98/11921 | 3/1998 |
| WO | 2003/026786 | 4/2003 |
| WO | 2005/027954 | 3/2005 |
| WO | 2006/002873 | 1/2006 |
| WO | 2014/082958 | 6/2014 |
| WO | 2015/136538 | 9/2015 |
| WO | 2015136538 A1 | 9/2015 |

OTHER PUBLICATIONS

Australian Patent Office Examination Report corresponding to AU 2018201339; dated Dec. 4, 2018 (3 pages).
European Examination Report corresponding to EP 16784310.1; dated Apr. 22, 2021 (7 pages).
Jansen et al. "Tumor Metabolism and Perfusion in Head and Neck Squamous Cell Carcinoma: Pretreatment Multimodality Imaging With 1H Magnetic Resonance Spectroscopy, Dynamic Contrast-Enhanced MRI, and [18F]FDG-PET" International Journal of Radiation Oncology, Biology, Physics, 82(1):299-307 (2012).
European Patent Office Examination Report, EP 16779304.1, dated Oct. 2017.
U.S. Patent and Trademark Office, Non-Final Office Action, U.S. Appl. No. 15/461,759, dated Sep. 19, 2017.

(Continued)

Primary Examiner — Michael G. Hartley
Assistant Examiner — Jagadishwar R Samala
(74) Attorney, Agent, or Firm — Myers Bigel, P.A.

(57) ABSTRACT

Ascorbate or a pharmaceutically acceptable salt thereof is described for use in carrying out a method, or for the preparation of a medicament for carrying out a method, of enhancing a magnetic resonance imaging (MRI) image of a body or body region such as an organ or organ region in a subject. The method is carried out by parenterally administering ascorbate or a pharmaceutically acceptable salt thereof to the subject in an MRI image-enhancing amount; and then generating, by MRI of the subject, an image of the body or body region. The ascorbate or pharmaceutically acceptable salt thereof enhances the MRI image.

15 Claims, 11 Drawing Sheets

(56) References Cited

OTHER PUBLICATIONS

European Patent Office Examination Report, EP 16779304.1, dated Feb. 26, 2018, 4 pages.
Office Action, U.S. Appl. No. 15/461,759, dated Mar. 14, 2016, 9 pages.
International Search Report and Written Opinion, PCT/US2016/054478, dated Dec. 15, 2016.
International Search Report and Written Opinion, PCT/US2016/054481, dated Dec. 14, 2016.
Sreevja V et al. Water-dispersible ascorbio-add-coated magnetite nanoparticles for contrast enhancement in MRI. Applied Nanoscience. Jul. 22, 2015; 5(4): 435-441.
Hayashi K et al. Superparamagnetic nanoparticle clusters for cancer theranostics combining magnetic resonance imaging and hyperthermia treatment. Theranostics. Apr. 23, 2013; 3(6): 366-376.
Biological Therapies. Product information—Sodium ascorbate solution 112,49 mg/ml. Jan. 1, 2011: 11 pp. Retrieved from the Internet Dec. 12, 2016: URL:http//www.hugogalindosalom.com/images/pdf/inserto.pdf; 9 pp.
Chan KW et l. Natural D-glucose as a biodegradable MRI contrast agent for detecting cancer. Magnetic Resonance in Medicine. Dec. 2012; 68(6): 1764-1773.
Yadav NN et al. Natural D-glucose as a biodegradable MRI relaxation agent. Magnetic Resonance in Medicine. Sep. 2014; 72(3): 823-828.
Bors Wand Buettner GR. The vitamin C radical and its reactions. Vitamin C in Health and Disease, ed. by L. Packer and J. Fuchs, Marcel Dekker, Inc., New York, Chapter 4. 1997, pp. 75-94.
Bushong Sand Clarke G. Perfusion imaging, Magnetic Resonance Imaging: Physical and Biological Principles. Mosby, 4th Ed. Chapter 24. 2014, pp. 345-352.
Lachapelle MY and Drouin G. Inactivation dates of the human and guinea pig vitamin C genes. Genetica. 2011; 139 (2): 199-207.
Hediger MA. New view at C. Nat. Med. May 2002; 8(5): 445-446.
Material Safety Data Sheet. Ascorbic acid MSDS. Science Lab.com. 5 pp. Retrieved from internet May 24, 2017.
May JM et al. Recycling of vitamin C from its oxidized forms by human endothelial cells. Biochim. Biophys. Acta. May 2003; 1640(2-3): 153-161.
Savini I et ai.SVCT1 and SVCT2: key proteins few vitamin C uptake. Amino Acids. Apr. 2008, 34(3): 347-355.
Rumsey SC et al. Glucose transporter isoforms GLUT1 and GLUT3 transport dehydrascorbic acid. J. Biol. Chem. Jul. 1997; 272(30): 18982-18989.
Oreopoulos DG et al. Renal excretion of ascorbic acid: effect of age and sex. JAm Coli Nutr. Oct. 1993;12(5): 537-542. Abstract only.
Levine M et al. Vitamin C pharmacokinetics in healthy volunteers: Evidence for a recommended dietary allowance. Proc Nat Acad Sci USA. Oct. 1993; 93(8): 3704-3709.
Hoffer LJ et al. Phase I clinical trial of i.v. ascorbic acid in advanced malignancy. Ann Oneal. 19: 1969-1974, 2008.
Chen Q et al. Pharmacologic doses of ascorbate act as a prooxidant and decrease growth of aggressive tumor xenografts in mice. Proc Natl Acad Sci USA. Aug. 2008;105(32): 11105-11109.
Carver JP and Richards RE. A General 2-site solution for chemical exchange produced dependence of T2 upon the Carr-Purcell pulse separation. J. Magn. Reson. 1972, 6: 89-106.
Hills BP et al. N.M.R. studies of water proton relaxation in Sephadex bead suspensions. Molecular Physics. 1989; 67(1): 193-208.
Liepinsh E and Otting G. Proton exchange rates from amino acid side chains-implication for image contrast. Magn Reson Med. 1996; 35(1): 30-42.
Lascola CD et al. MR contrast from ascorbic acid (vitamin C) in phantoms and in vivo. International Society for Magnetic Resonance in Medicine. 2010 ISMRM Meeting #40, May 1-7, 2010, Stockholm, Sweden.
Jansanoff A. MRI contrast agents for functional molecular imaging of brain activity. Curr Opin Neurobiol. Oct. 2007; 17(5): 593-600.
Meglumine. Wikipedia, retrieved Jan. 12, 2016, 1 p.
Van Noorden R. The medical testing crisis. Nature. Dec. 12, 2013; 504: pp. 202-204.
Chinese Office Action corresponding to CN 201680003013.1, dated Mar. 20, 2020 (12 pages including English Translation).
Chinese Supplementary Search Report corresponding to CN 201680003013.1 (2 pages).

* cited by examiner $K_{obs}$ (7.4) = 1.4 X 10$^5$ M$^{-1}$ s$^{-1}$

THIS RATE CONSTANT INCREASES BY A FACTOR OF ≈10 WHEN PHOSPHATE IS PRESENT.*

T2WI FSE

2 MIN       10 MIN

T2WI

RARE T2 MAP

PRE DOSE       30 MIN

60 MIN       90 MIN

CONTRAST AGENTS FOR MAGNETIC RESONANCE IMAGING

RELATED APPLICATIONS

This application is a continuation of and claims priority to U.S. patent application Ser. No. 15/812,013, filed Nov. 14, 2017, now allowed, which is a continuation of U.S. patent application Ser. No. 15/461,628, filed Mar. 17, 2017, now U.S. Pat. No. 10,111,970, which is a continuation under 35 U.S.C. 111(a) of PCT/US2016/054478, filed Sep. 29, 2016, which in turn claims the benefit of U.S. Provisional Patent Application Ser. No. 62/234,986, filed Sep. 30, 2015, and U.S. Provisional Patent Application Ser. No. 62/291,138, filed Feb. 4, 2016, the disclosure of each which is incorporated by reference herein in its entirety.

FIELD OF THE INVENTION

The present invention concerns compositions useful as contrast agents for magnetic resonance imaging and methods of use thereof.

BACKGROUND OF THE INVENTION

Magnetic resonance imaging (MRI) produces exquisite renderings of human anatomy and pathology at high spatial resolution. To increase diagnostic sensitivity and specificity for MRI, such as with imaging for cancer, infection, neurological and heart diseases, contrast material is often administered intravenously before and/or during imaging to improve signal.

The most common MRI contrast material is based on molecular complexes containing the paramagnetic metal gadolinium (Gd). In the U.S., all nine FDA-approved MRI contrast agents are Gd-based. Gd possesses strong "paramagnetism" that results in a locally increased MRI signal on $T_1$-weighted images. However, Gd-based contrast agents can cause a rare but severely debilitating condition called nephrogenic systemic fibrosis (NSF), a syndrome involving widespread fibrosis of the skin, joints, eyes, and internal organs. The WHO and FDA have issued restrictions on the use of these agents in patients with renal insufficiency/failure, with the FDA mandating a "black box" warning on all commercial media containing gadolinium. As a consequence, millions of patients in the U.S., and many more worldwide, are no longer able to receive contrast material for MRI, severely limiting detection and characterization for several diseases.

Other paramagnetic complexes, used more rarely either as investigational or as "off-label," are usually based on large iron oxide-based nanoparticles developed and marketed as intravenous iron replacement therapy (e.g., FERAHEME® (ferumoxytol) injection). The use of these complexes for MRI is limited, however, by their large molecular size, which confines these agents to the blood pool until they are finally cleared by the reticuloendothelial system (i.e., macrophages, liver, spleen).

U.S. Patent Application Publication 2014/0154185 to Van Zijl et al. discusses the use of parenteral glucose to enhance MRI. See also Yadav N N, Xu J, Bar-Shir A, Qin Q, Chan K W, Grgac K, Li W, McMahon M T, van Zijl P C, Natural D-glucose as a biodegradable MRI contrast agent for detecting cancer. Magn Reson Med. 2012 December; 68(6):1764-73; Yadav N N, Xu J, Bar-Shir A, Qin Q, Chan K W, Grgac K, Li W, McMahon M T, van Zijl P C, Natural D-glucose as a biodegradable MRI relaxation agent. Magn Reson Med. 2014 September; 72(3):823-28.

There remains a need for alternative contrast agents useful for MRI scanning technologies.

SUMMARY OF THE INVENTION

Provided herein are methods useful for magnetic resonance imaging (MRI) using parenteral ascorbate (Vitamin C) as a contrast agent for the detection and characterization of perfusion, metabolism, and oxidative stress in human and non-human tissues without the need for radioactivity or chemical labeling. After parenteral administration, time-dependent magnetic resonance (MR) signal changes are detected in tissues where ascorbate is taken up and/or passes through. These MRI signal changes are detectable using routine spin echo or gradient echo-based $T_2$-weighted MRI sequences and quantifiable with $T_2$ mapping. Other less common acquisition techniques sensitive to spin-spin relaxation may also be used to encode MR signals.

Thus, provided herein is a method of enhancing an MRI image of a body or body region, such as an organ or organ region in a subject, which method includes parenterally administering (e.g., intravenous, intraperitoneal, intraarterial, intraosseous, or intrathecal administration) ascorbate or a pharmaceutically acceptable salt thereof to said subject in an MRI image-enhancing amount; and then generating, by MRI of the subject, an image of said body or body region, whereby the ascorbate or pharmaceutically acceptable salt thereof enhances the MRI image.

In some embodiments, the MRI image is generated during, or up to 5, 10, 30, 40, 60, 90 or 120 minutes after, the parenterally administering of ascorbate or pharmaceutically acceptable salt thereof.

In some embodiments, the ascorbate or pharmaceutically acceptable salt thereof is sodium ascorbate, meglumine ascorbate, or a mixture thereof (e.g., meglumine ascorbate and sodium ascorbate in a molar or millimolar (mM) ratio of from 10:90, 20:80, 30:70, or 40:60, up to 90:10, 80:20, 70:30, or 60:40 (meglumine ascorbate:sodium ascorbate)).

Further provided is the use of ascorbate or a pharmaceutically acceptable salt thereof for carrying out a method as taught herein, or for the preparation of a medicament or imaging agent for carrying out a method as taught herein.

The present invention is explained in greater detail in the drawings herein and the specification set forth below. The disclosures of all United States patent references cited herein are to be incorporated by reference herein in their entirety.

BRIEF DESCRIPTION OF THE DRAWINGS

FIG. 1A, Ascorbate is a di-acid, however at pH 7.4, 99% is present as the mono anion (AscH$^-$). Ascorbate radical (Asc$^{\cdot-}$) is present at equilibrium (but also at much lower concentrations) with oxidized and reduced forms of ascorbate. FIG. 1B, The dismutation of Asc$^{\cdot-}$ is the principal route of its transformation, with a rate constant ($k_{obs}$) that falls into the "intermediate" proton exchange rate on the NMR timescale. This rate constant can increase by a factor of 10 in the presence of phosphate (Bors W, Buettner G R. (1997) The vitamin C radical and its reactions in *Vitamin C in Health and Disease*, ed. by L. Packer and J. Fuchs, Marcel Dekker, Inc., New York, Chapter 4, pp 75-94).

FIG. 3A, shows quantitative $T_2$ mapping in 5 phantoms with progressively increasing ascorbate (AA) concentration. Statistically significant "negative $T_2$ contrast" (signal loss) is seen as low 1-5 mM as compared to control (phosphate-buffered saline) with conventional fast spin echo (FSE) acquisition. Sensitivity is therefore at the lower end of expected tissue/cellular concentrations following pharmacological doses of ascorbate in high uptake tissues (e.g., tumors and brain, 10-30 mM). This also does not include any synergistic effect from tissue oxidative substrates or exchange catalysts. FIG. 3B, shows the synergistic effect of $H_2O_2$ on ascorbate $T_2$ enhancement. $H_2O_2$, which rises to 100-200 micromolar in brain and tumors in vivo following parenteral ascorbate, produces a marked synergism on the $T_2$ contrast effect from ascorbic acid. The synergistic effect slowly diminishes over time in phantoms over 30 min as above, but will be sustained in vivo as long as $H_2O_2$ is produced following pharmacological ascorbate doses. FIG. 3C, demonstrates the influence of pH on ascorbate's $T_2$ effect, which is maximized at neutral/physiological pH (7.0-7.4). This result is consistent with prior studies on the rate kinetics of ascorbate disproportionation with its radical and oxidized form at equilibrium (FIGS. 1A-1B). FIG. 3D, reveals a marked synergistic effect when ascorbate (Asc) is salified (salted) with meglumine (Meg), an amine sugar derivative of sorbital that is commonly employed as an excipient in several FDA-approved drug and contrast formulations.

FIG. 9A, shows a conventional single slice axial FSE T2WI image through the midbrain of a normal C57 black mouse, and the two images on the right demonstrate a 'first pass' extraction of contrast change during and following ascorbate administration i.v. T2 signal in brain tissue immediately following, and 10 minutes after, ascorbate administration is acquired and then subtracted from the T2 brain signal acquisition pre ascorbate administration. Since ascorbate produces a decrease in signal intensity, subtraction from the higher signal pre-dose scan results in a net positive 'map' of flow-through perfusion (blood flow) through brain tissue. At 10 minutes, the perfusion effect has nearly resolved and early signal intensity changes related to tissue uptake are beginning to be observed. FIG. 9B, show the signal changes due to tissue uptake of high-dose ascorbate. Color-lute maps of signal intensity are not subtracted from the pre-dose scan and therefore show the expected decreases in T2 signal over time, maximized between 30-60 min in normal C57 mice.

FIG. 11A depicts the two primary imaging planes, coronal and axial, for rat heart imaging at 7 T. FIG. 11B shows transient decrease in T2 signal intensity throughout the left ventricle with initial bolus of ascorbate injection i.v.

FIG. 12A, Fast spin echo (FSE) T2 images before and after 60 min slow infusion of ascorbate show dramatic signal intensity differences throughout the brain parenchyma. FIG. 12B and FIG. 12C respectively show normalized signal intensity changes and quantitative relaxivity measurements are shown for both guinea cerebral cortex (Cx) and basal ganglia (BG) after administration of three different ascorbate formulations.

DETAILED DESCRIPTION OF THE PREFERRED EMBODIMENTS

Figure 1A:
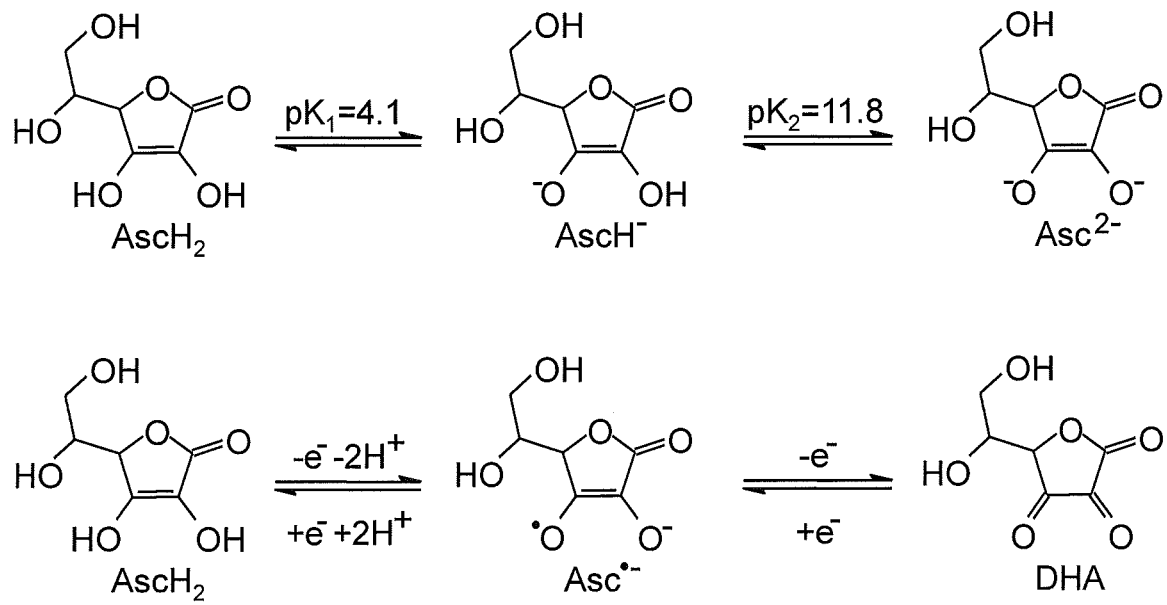
FIGS. 1A-1B. Ascorbate and dismutation of the ascorbate radical.

Subjects for the present invention are, in general, mammalian subjects, including both human subjects and animal subjects (e.g., dogs, cats, rabbits, cattle, horses, etc.) for research or veterinary purposes. Subjects may be male or female and may be any age, including neonate, infant, juvenile, adolescent, adult, and geriatric subjects.

Magnetic resonance imaging (MRI) is known, and may be carried out by commercially available equipment, and by techniques known in the field. See, e.g., S. Bushong and G. Clarke, *Magnetic Resonance Imaging: Physical and Biological Principles* (Mosby, 4$^{th}$ Ed. 2014). In some embodiments, the MRI is perfusion (e.g., blood flow) imaging. In some embodiments, the MRI is metabolism imaging. Metabolism imaging may be used as a diagnostic biomarker analogous to 18F FDG PET, including, but not limited to, identification/characterization of tumors or dysfunctional tissues demonstrating hyper- or hypo-metabolism.

"Body or body region" that may be imaged with MRI as taught herein includes the body or any region of the body of a subject, such as an organ or organ system, soft tissue, bone, etc., or any portion thereof. Examples of body regions include, but are not limited to, head, neck, thorax, abdomen, pelvis, limb(s), muscle, fat, other soft tissues, bone, etc. Examples of organs include, but are not limited to, adrenal gland, pituitary, thymus, corpus luteum, retina, brain, spleen, lung, testicle, lymph nodes, liver, thyroid, small intestinal mucosa, leukocytes, pancreas, kidney, salivary gland tissue, heart, etc.

"Enhancing" an MRI image as used herein is inclusive of facilitating the MRI visualization by enhancing the contrast of structures or fluids in an MRI signal.

An "MRI contrast agent" is a substance that can enhance the contrast of structures or fluids within the body during an MRI scan. Examples include, but are not limited to, paramagnetic contrast agents such as gadolinium(III) containing agents or manganese chelates, and superparamagnetic agents such as iron platinum particles. See also U.S. Patent Application Publication Nos. 2014/0350193 to Axelsson et al.; 2014/0234210 to Lin et al.

"Parenteral administration" as used herein includes, but is not limited to, intravenous, subcutaneous, intramuscular, intraperitoneal, intraarterial, intraosseous, or intrathecal administration, e.g., through injection or infusion. As a non-limiting example, intraperitoneal or other parenteral administration may be used where intravenous (i.v.) access is difficult for a subject (e.g., low blood pressure), or the route of administration otherwise would result in a suitable MRI image.

MR Imaging and Clinical Application of Contrast Media.

Clinical magnetic resonance imaging (MRI) generates high-resolution images of the body through the acquisition of proton ($^1$H) NMR signals from water and macromolecules in tissue. For "$T_1$-weighted" MR images, signal intensity increases in regions where longitudinal relaxation rate (spin lattice relaxation rate, $1/T_1$) increases. With "T2-weighted" MRI, signal intensity decreases when transverse relaxation rate (spin-spin relaxation rate, $1/T_2$) increases. Both $T_1$ and $T_2$ weighted images are routinely acquired in virtually all clinical MRI studies.

Intravenous contrast agents are routinely administered in MRI to further increase $1/T_1$ or $1/T_2$, in an effort to better delineate diseased from normal tissue, improve anatomical definition, and enhance characterization of physiological or pathological function. Almost all currently approved MRI contrast agents are based on chelates of the lanthanide metal Gadolinium (Gd), with a smaller subset of angiographic and perfusion studies conducted using iron-oxide materials (e.g., Feraheme) off-label in patients with renal insufficiency/failure. Commercial Gd-based materials are used most commonly to increase $1/T_1$ in diseased tissue, where contrast material is prone to accumulate.

For tissue perfusion determinations with MRI, Gd-based agents or iron-oxide nanoparticles may be used, with acquisition strategies based on either $1/T_1$ or $1/T_2$ contrast, although $1/T_2$ contrast approaches are increasingly favored. Perfusion imaging is currently used clinically to characterize tumor aggressiveness, tumor response to therapy, and tissue viability in heart, brain and other organs.

Ascorbic Acid.

Ascorbic acid ("L-ascorbic acid," "ascorbate," "Vitamin C") is a naturally-occurring organic compound and an essential nutrient, with important properties as an antioxidant and co-factor in at least eight enzymatic reactions, including several collagen synthesis reactions that, when dysfunctional, result in the most conspicuous symptoms of scurvy. Most mammals make ascorbic acid in the liver, where the enzyme L-gulonolactone oxidase converts glucose to ascorbic acid. In humans, higher primates, guinea pigs and most bats, however, a mutation results in low or absent L-gulonolactone oxidase expression, so that ascorbate must be consumed in the diet (Lachapelle, M. Y.; Drouin, G. (2010). "Inactivation dates of the human and guinea pig vitamin C genes". *Genetica* 139 (2): 199-207). In all animal species, L-ascorbic acid/ascorbate is the most abundant intracellular antioxidant, with intracellular concentrations capable of reaching 10-30 mM in tumors, brain cells, and some other tissues. Those tissues that accumulate over 100 times the level in blood plasma of vitamin C include the adrenal glands, pituitary, thymus, corpus luteum, and retina. Those with 10 to 50 times the concentration include brain, spleen, lung, testicle, lymph nodes, liver, thyroid, small intestinal mucosa, leukocytes, pancreas, kidney, and salivary glands (Hediger M A (May 2002). "New view at C". *Nat. Med.* 8 (5): 445-6).

Dietary excesses of vitamin C are not absorbed, and excesses in the blood are rapidly excreted in the urine. Vitamin C exhibits remarkably low toxicity, with an $LD_{50}$ in rats generally accepted at ~11.9 grams per kilogram of body weight by forced gavage. The mechanism of death from such doses (1.2% of body weight, or 0.84 kg for a 70 kg human) is unknown, but may be mechanical rather than chemical ("Safety (MSDS) data for ascorbic acid". Oxford University. Oct. 9, 2005. Retrieved Feb. 21, 2007). The $LD_{50}$ in humans is uncertain given the lack of any accidental or intentional poisoning death data. The rat $LD_{50}$ is therefore used as a guide for human toxicity.

Figure 1B:
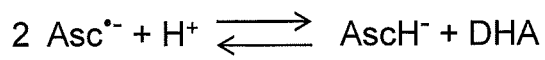

At physiological pH, 99% of ascorbic acid is present as the mono anion (FIG. 1A). The chemistry, and therefore imaging properties, of vitamin C are dominated by this moiety. As a donor antioxidant, the mono anion donates a hydrogen atom (H˙ or H$^+$+e$^-$) to an oxidizing radical to produce a resonance-stabilized tricarbonyl ascorbate free radical, Asc˙$^-$ (FIG. 1B). The dismutation reaction of Asc˙$^-$ back to reduced or oxidized ascorbate is the principal route of elimination in vitro. This process is supplemented in vivo by enzymes that aid in ascorbate recycling (May J M, Qu Z C, Neel D R, Li X (May 2003). "Recycling of vitamin C from its oxidized forms by human endothelial cells". *Biochim. Biophys. Acta* 1640 (2-3): 153-61). Dismutation of the radical to either ascorbate or dehydroascorbate occurs via loss or gain of hydrogen, which serves as either the electron carrier or the more conventional cation. Also, the rate constant of ascorbic radical dismutation is $10^5$-$10^6$ $M^{-1}s^{-1}$, so that hydrogen exchange accompanying dismutation also occurs at the same rate. On the NMR timescale, these "intermediate" exchange rates are optimal for altering $^1$H spin-spin relaxation.

Ascorbate Transport and Excretion.

Ascorbic acid is absorbed in the body by both active transport and simple diffusion. The two major active transport pathways are sodium-ascorbate co-transporters (SVCTs) and hexose transporters (GLUTs). SVCT1 and SVCT2 import the reduced form of ascorbate across the plasma membrane (Savini I, Rossi A, Pierro C, Avigliano L, Catani M V (April 2008). "SVCT1 and SVCT2: key proteins for vitamin C uptake". *Amino Acids* 34 (3): 347-55), whereas GLUT1 and GLUT3 glucose transporters transfer the oxidized form, dehydroascorbic acid (Rumsey S C, Kwon O, Xu G W, Burant C F, Simpson I, Levine M (July 1997). "Glucose transporter isoforms GLUT1 and GLUT3 transport dehydroascorbic acid". *J. Biol. Chem.* 272 (30): 18982-

9). Although dehydroascorbic acid concentrations are low in plasma under normal conditions, the oxidized molecule is absorbed at much higher rates across GLUT1 and 3 than the reduced form is across the SVCTs. When ascorbate concentrations are pharmacologically elevated, dehydroascorbate concentration also increases, enabling marked absorption where GLUT transporters exist in high copy such as brain (and blood brain barrier) and tumor cells. Once transported, dehydroascorbic acid is rapidly reduced back to ascorbate.

Ascorbate concentrations over the renal re-absorption threshold pass freely into the urine and are excreted with a half-life of about 30 minutes. At high dietary doses (corresponding to several hundred mg/day in humans) the renal resorption threshold is 1.5 mg/dL in men and 1.3 mg/dL in women (Oreopoulos D G, Lindeman R D, VanderJagt D J, Tzamaloukas A H, Bhagavan H N, Garry P J (October 1993). "Renal excretion of ascorbic acid: effect of age and sex". *J Am Coll Nutr* 12 (5): 537-42). Ascorbate that is not directly excreted in the urine or destroyed by other body metabolism is oxidized by L-ascorbate oxidase and removed.

Without wishing to be bound by theory, the mechanism of ascorbate signal change without paramagnetism, which is also described as "$T_2$-weighted contrast," is based on enhancement of the water proton ($^1H$) spin-spin relaxation rate $1/T_2$ (or reciprocally, spin-spin relaxation time, $T_2$), as solvent water protons are exchanged with hydroxyl protons on ascorbate molecules. The effect of proton exchange on $T_2$ contrast is amplified further by the dismutation reaction of the ascorbate radical at physiological pH. Ascorbate oxidation and ascorbate radical dismutation are, in turn, driven by the co-presence of oxidizing substrates such as hydrogen peroxide ($H_2O_2$) and/or hydrogen ("proton") exchange catalysts.

Ascorbate, especially in the presence of, and co-formulated with, spin-spin exchange catalysts (for example, simple sugars, sugar alcohols or amino acids) is a safe and biodegradable MRI contrast agent that requires neither the use of metal-based (e.g., gadolinium or iron) contrast material nor ionizing radiation. The technique enables assessment of tissue perfusion as well as high-resolution molecular characterization of tissue viability and metabolism that is analogous to $^{18}F$-FDG PET. The latter is possible by virtue of ascorbate's uptake (via dehydroascorbate) into cells through the same glucose transport mechanisms that take up $^{18}F$-FDG (i.e., GLUT 1 and 3 transporters) (Rumsey S C, Kwon O, Xu G W, Burant C F, Simpson I, Levine M (July 1997). "Glucose transporter isoforms GLUT1 and GLUT3 transport dehydroascorbic acid". *J. Biol. Chem.* 272 (30): 18982-9).

Potential applications for ascorbate MRI include several clinical scenarios where PET scanning has already proven valuable but also where improvements in methodology will yield further clinical benefit. These scenarios include diagnostic studies for cancer, neurological disease (e.g., dementia, TBI and epilepsy) and cardiovascular imaging. Heart studies using Tc99m-labeled agents (e.g., Tc-99m sestimibi or "Cardiolite") represent a particularly noteworthy diagnostic application in dire need of an alternative strategy given the expected contraction of the world's Tc-99m supply over the next 3-5 years. Myocardial perfusion and viability imaging with Tc-99m-related agents is an essential and widely performed procedure, yet no financially feasible solution has been offered to replace these Tc-99m-dependent agents.

The use of high-dose parenteral ascorbate as adjunctive chemotherapy for several malignancies is the subject of on-going clinical cancer trials investigating this vitamin. Ascorbate MRI as taught herein may thus be useful to inform the study and application of this chemotherapeutic, coupling high resolution MR imaging to therapeutic administration that may enable real-time optimization of delivery and tumor response assessment.

Ascorbate is now understood to have a pharmacokinetic profile that resembles vancomycin. Biodistribution of oral ascorbate is under tight control, with plasma concentrations rarely exceeding 200 μM even at oral doses more than 100 times the recommended daily allowance (Levine M, Conry-Cantilena C, Wang Y, Welch R W, Washko P W, Dhariwal K R, Park J B, Lazarev A, Graumlich J F, King J, Cantilena L R (April 1996). "Vitamin C pharmacokinetics in healthy volunteers: evidence for a recommended dietary allowance". *Proc. Natl. Acad. Sci. U.S.A.* 93 (8): 3704-9). Ascorbate administered intravenously, however, bypasses these tight control systems, with plasma concentrations of 10 mM or higher achievable. Plasma concentrations higher than 10 mM are safely sustained in humans for up to 4 hours with remarkably low toxicity (Hoffer L J., Levine M., Assouline S., Melnychuk D., Padayatty S J., Rosadiuk K., Rousseau C., Robitaille L., and Miller W H., Jr., Phase I clinical trial of i.v. ascorbic acid in advanced malignancy. *Ann Oncol* 19: 1969-1974, 2008).

More recent studies have shown than pharmacological ascorbate concentrations achieved through intravenous infusion results in the formation of ascorbate radicals and the production of hydrogen peroxide ($H_2O_2$) at concentrations cytotoxic to cancer cells but not normal cells (Chen Q., Espey M G., Sun A Y., Pooput C., Kirk K L., Krishna M C., Khosh D B., Drisko J., and Levine M. Pharmacologic doses of ascorbate act as a prooxidant and decrease growth of aggressive tumor xenografts in mice. Proc Natl Acad Sci USA 105: 11105-11109, 2008). Several preclinical xenograft studies have demonstrated remarkable growth inhibition with high-dose parenteral ascorbate, and even more recent clinical trials likewise show promising results that also confirm an excellent safety profile. In preclinical mechanistic studies, the production of $H_2O_2$ is a salient feature. Microdialysis measurements reveal that $H_2O_2$ concentrations rise to >100s μM after high-dose parenteral ascorbate, with both ascorbate and $H_2O_2$ reaching their highest concentrations in tumors and brain regions such as striatum (Chen Q., Espey M G., Sun A Y., Pooput C., Kirk K L., Krishna M C., Khosh D B., Drisko J., and Levine M. Pharmacologic doses of ascorbate act as a prooxidant and decrease growth of aggressive tumor xenografts in mice. Proc Natl Acad Sci USA 105: 11105-11109, 2008).

Ascorbate in a pharmaceutically acceptable carrier (e.g., sterile water or saline) as a formulation for parenteral administration useful for carrying out the present invention are known, for example for the treatment of scurvy. Examples of suitable formulations include, but are not limited to, a sterile solution of ascorbic acid in water for injection, where each milliliter of water contains: ascorbic acid 500 mg, disodium edetate 0.25 mg, sodium hydroxide 110 mg, in water for Injection q.s. pH (range 5.5 to 7.0) adjusted with sodium bicarbonate and sodium hydroxide. Formulations suitable for parenteral administration may include a pharmaceutically acceptable salt of ascorbate (e.g., sodium salt or meglumine salt), such as a sterile solution thereof, and may also include pH buffers such as bicarbonate ($HCO_3^-$) and/or phosphate ($PO_4$).

The term "pharmaceutically acceptable" as used herein means that the compound or composition is suitable for administration to a subject to achieve the treatments described herein, without unduly deleterious side effects in light of the severity of the disease and necessity of the treatment.

The present invention is explained in greater detail in the following non-limiting examples.

In Vitro Examples

Ascorbate Enhancement of Spin-Spin Relaxation Rate, $1/T_2$

Previous studies have reported on the NMR/MRI contrast effects on $T_2$-weighting arising from exchange of bulk water protons with mobile protons of low molecular weight solutes and macromolecules (e.g., —$NH_2$, —OH, —SH, —NH). The contrast effect on $1/T_2$ from this proton exchange is described as follows:

$$\frac{1}{T_2} = \frac{1}{T_{2a}} + f_{CR}(P_b, \delta\omega_b, k, T_{2b}, \tau)$$

Bulk water is related to $_a$ and exchangeable protons (e.g., from an ascorbate OH group) to $_b$. $f_{CR}$ is a closed function with five parameters, derived from Carver and Richards and refined by Hill et al. (Carver, J. P.; Richards, R. E. J. General 2-Site Solution For Chemical Exchange Produced Dependence Of T2 Upon Carr-Purcell Pulse Separation J. Magn. Reson. 1972, 6, 89-105; Hills, B. P.; Wright, K. M.; Belton, P. S. N.M.R studies of water proton relaxation in Sephadex bead suspensions Mol. Phys. 1989, 67, 1309-1326). For the hydroxyl protons of ascorbate, $P_b$ would be the fraction of exchangeable protons, κ is the exchange rate between exchangeable protons and water protons, $\delta\omega_b$ is the chemical shift between hydroxyl and bulk water protons, and $T_{2b}$ is the local spin-spin relaxation time of hydroxyl protons. τ is the inter-pulse (90°-180°) spacing in the $T_2$-weighted acquisition sequence.

An essential but often neglected parameter influencing proton exchange on $T_2$ contrast is the role of exchange catalysis (Liepinsh E and Otting, G Proton exchange rates from amino acid side chains—implications for image contrast. Magn Reson Med. 1996 35(1): 30-42). The rate constant k for proton exchange between OH or NH groups and water can be described by $$k = k_a[H^+] + k_b[OH^-] + \Sigma k_c [\text{catalyst}]^y$$

$K_a$, $K_b$ and $K_c$ denote the exchange rate constants due to catalysis by $H^+$, $OH^-$ and other exchange catalysts, respectively. The exponent y is 1 or 2 depending on the mechanism of a given exchange catalyst. The rate constants $K_a$ and $K_b$ can be calculated in turn by:

$$k_{a,b} = k_D \frac{1}{1 + 10^{pKD - pKA}}$$

where $K_D$ is the rate constant for diffusion controlled encounter of the proton donor and acceptor (~$10^{10}$ $mol^{-1}s^{-1}$), and $pK_D$ and $pK_A$ are the pK values of the proton donor and acceptor. Although $pK_{H3O+}$ and $pK_{OH-}$=15.7, $K_c$ is more challenging to predict because of the nonlinear dependence of proton transfer on catalyst concentration. Nonetheless, efficient exchange catalysis at neutral pH is attained with at least a moderate difference between $pK_D$–$pK_A$ and a significant concentration of catalytically active acidic or basic forms of the exchange catalysts at physiological pH.

Thus $H_2O$, despite its high concentration, is an inefficient exchange catalyst at neutral pH because it's a relatively poor proton donor, with the $pK_D$ and $pK_A$ (for $H_3O^+$ and $OH^-$) are 15.7. On the other hand, recognized exchange catalysts in physiological conditions include organic phosphates, carbonates (e.g., bicarbonate, $HCO_3^-$), and molecules with carboxyl and amino groups (Liepinsh E and Otting, G Proton exchange rates from amino acid side chains—implications for image contrast. Magn Reson Med. 1996 35(1): 30-42). As shown below, another powerful catalyst not previously recognized is ascorbate, which possesses one hydroxyl group having a favorable $pK_A$=6.75 at the 4 position, as well as a disproportionation reaction at equilibrium with a $pK_A$=7.0. Thus ascorbate has the potential to not only 'self-catalyze', but should be an efficient catalyst of proton exchange for basic hydroxyl groups on sugars and other macromolecules.

Figure 2:
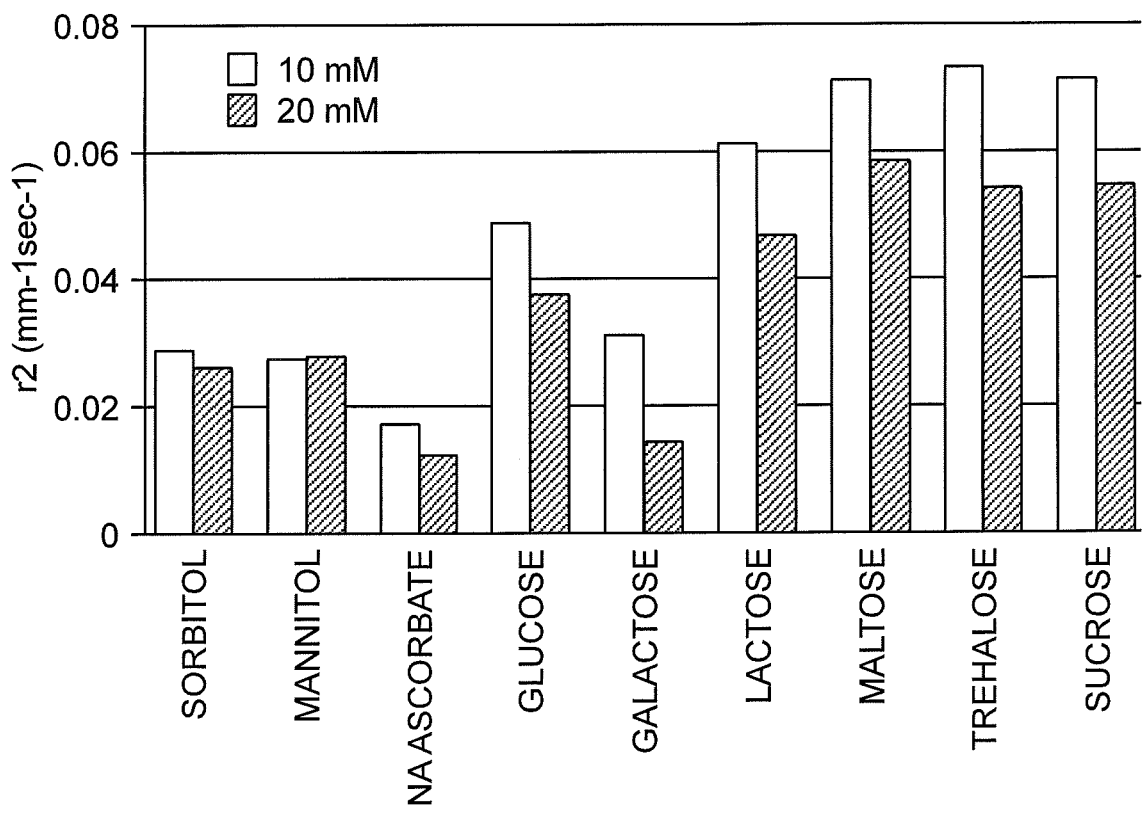
FIG. 2. $T_2$ relaxivity ($r_2$=mM$^{-1}$sec$^{-1}$) of sugars, sugar alcohols, and ascorbate Comparisons include both mono and disaccharides. As discussed in the text, note the diminishing contrast effect at higher concentration, believed secondary to self-association of like moieties and reduced proton exchange.

FIG. 2 shows a comparison on $T_2$ enhancement of pure solutions of several sugars, sugar alcohols, and ascorbate in deionized water at pH 7. Data are provided from quantitative $T_2$ mapping at 7 T using a RARE FSE protocol with at least 6 different echo times, at solute concentrations of 10 and 20 mM. As shown, $T_2$ relaxivity is roughly a function of the number of exchangeable OH protons available on each molecule, with disaccharides, as predicted, producing proportionally greater contrast effect than monosaccharides. Noteworthy is the nonlinear dependence on solute concentration, with relaxivity enhancement decreasing as concentration is increased, a phenomenon that is likely related to self-association of sugars in pure solutions. The latter is particularly relevant to observations described below, where overall $T_2$ effects are instead synergistically enhanced when ascorbate and sugars are combined together at higher total solute concentrations. Formulations combining ascorbate with mono or disaccharides provide a means to deliver higher concentrations of both species in order to increase $T_2$ contrast effects for MR imaging.

Figure 3A:
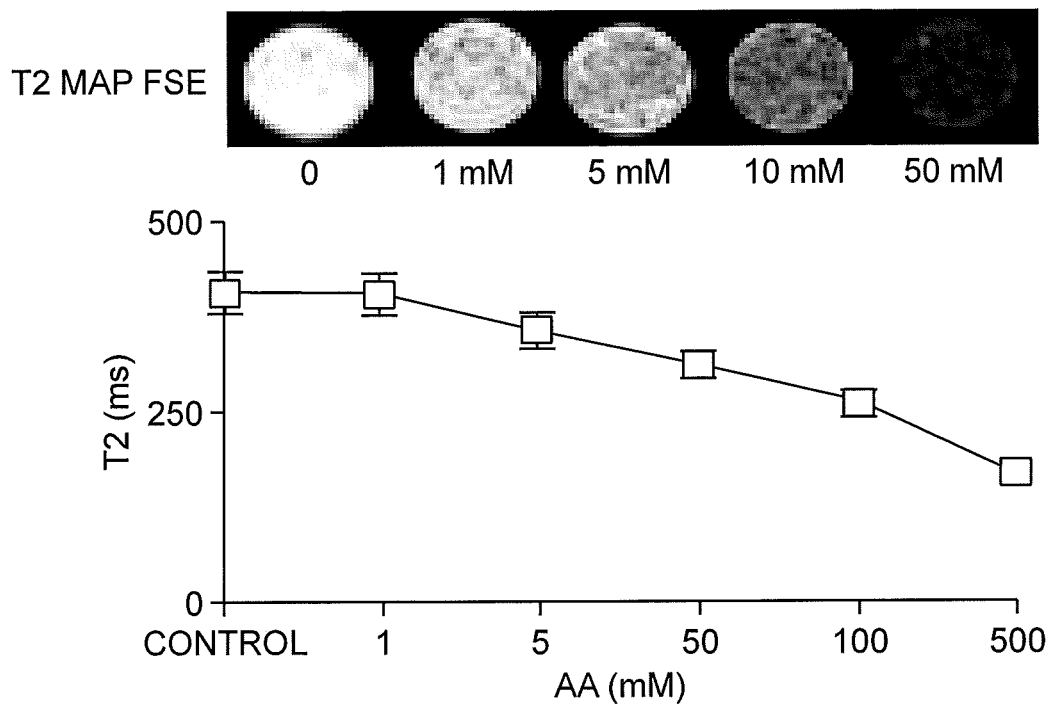
FIGS. 3A-3D. In vitro ("phantom") experiments on ascorbate spin-spin relaxation ($T_2$-weighted) MRI contrast.
Figure 3B:
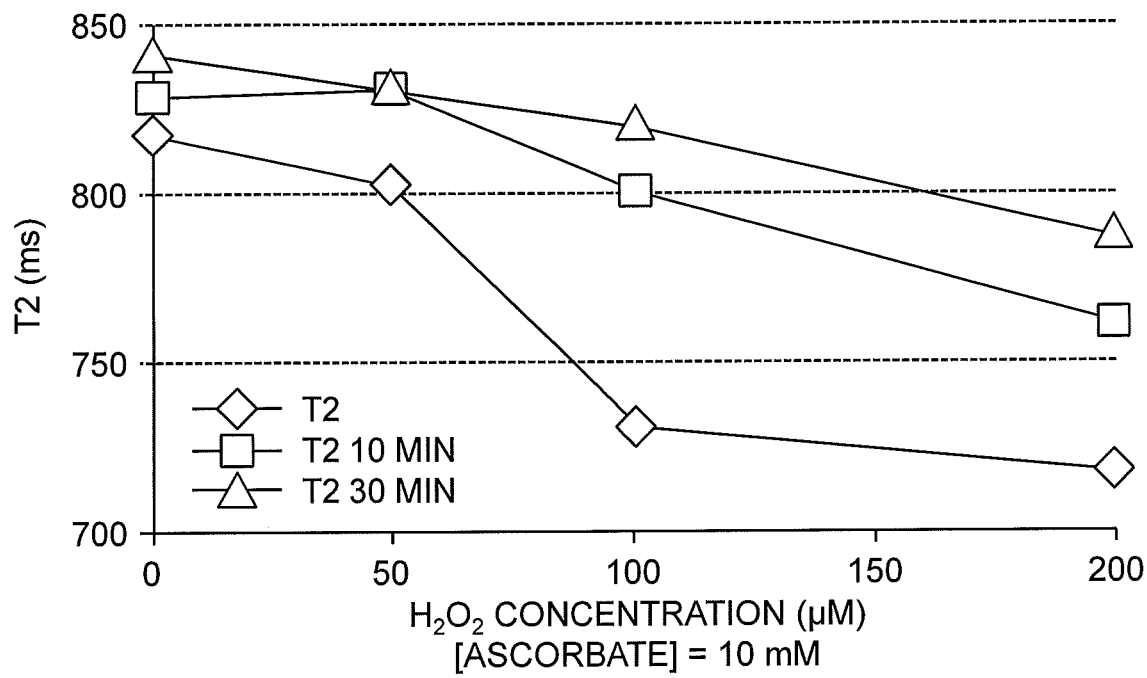
Figure 3C:
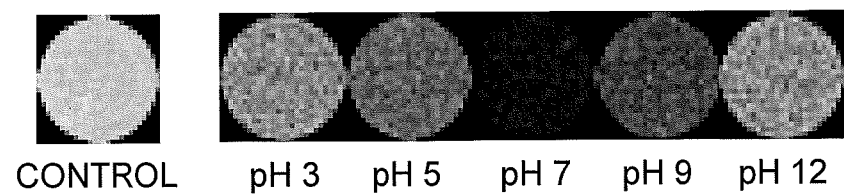
Figure 3C:
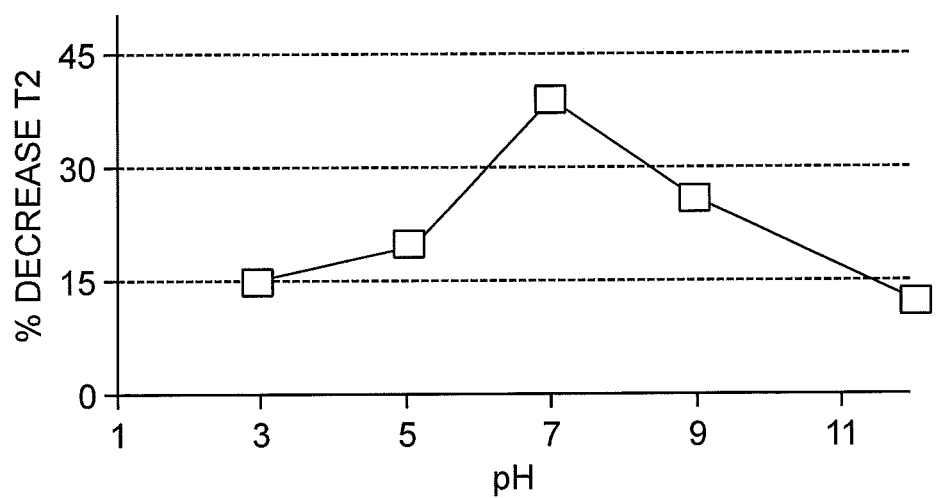

FIG. 3A depicts a more detailed demonstration of $T_2$ effects of pure ascorbate solutions at different concentrations at neutral pH. FIG. 3B reveals the marked enhancement of the $T_2$ effect when ascorbate is in the presence of only μM (i.e., physiological) concentrations of hydrogen peroxide ($H_2O_2$), which drives oxidation to dehydroascorbate as well as ascorbate radical dismutation. Although $H_2O_2$ is also considered an exchange catalyst in its own right, the dramatic effect observed on ascorbate-mediated $1/T_2$ enhancement when $H_2O_2$ is present at 100-fold less concentration than ascorbate suggests that proton exchange from $H_2O_2$-driven ascorbate oxidation/dismutation, rather than direct exchange from OH ascorbyl protons, is an important contributory mechanism responsible for $T_2$ changes. Further evidence of the contribution from dehydroascorbate oxidation/dismutation on proton exchange is depicted in FIG. 3C showing that the $1/T_2$ enhancement effect is by far the most significant at neutral pH where the reaction rate of ascorbate-dehydroascorbate disproportionation is also greatest.

Figure 3D:
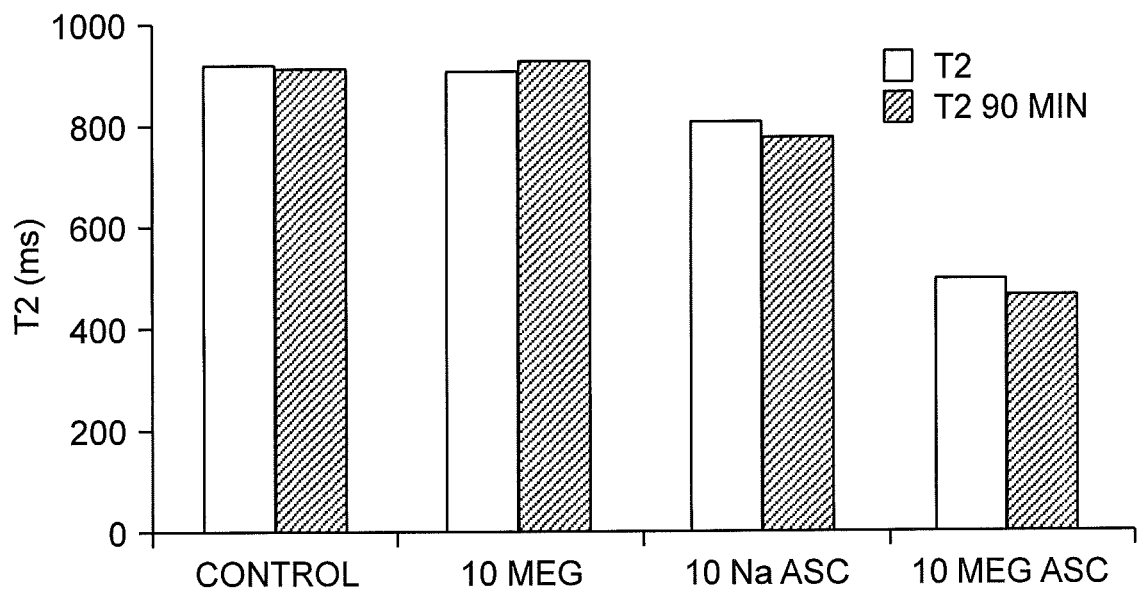

Data in FIG. 3D provides the first suggestion that exchange catalysis between ascorbate and an acceptor/donor molecule with an appropriate pK can markedly drive $1/T_2$ enhancement change. Data here compare solutions of ascorbate as sodium salt and as meglumine (aminosugar) salt. Here the $T_2$ contrast effect ($T_2$ relaxation in ms) is approximately 4 times greater with meglumine ascorbate as compared to either meglumine or ascorbate alone in water at neutral pH.

Figure 4:
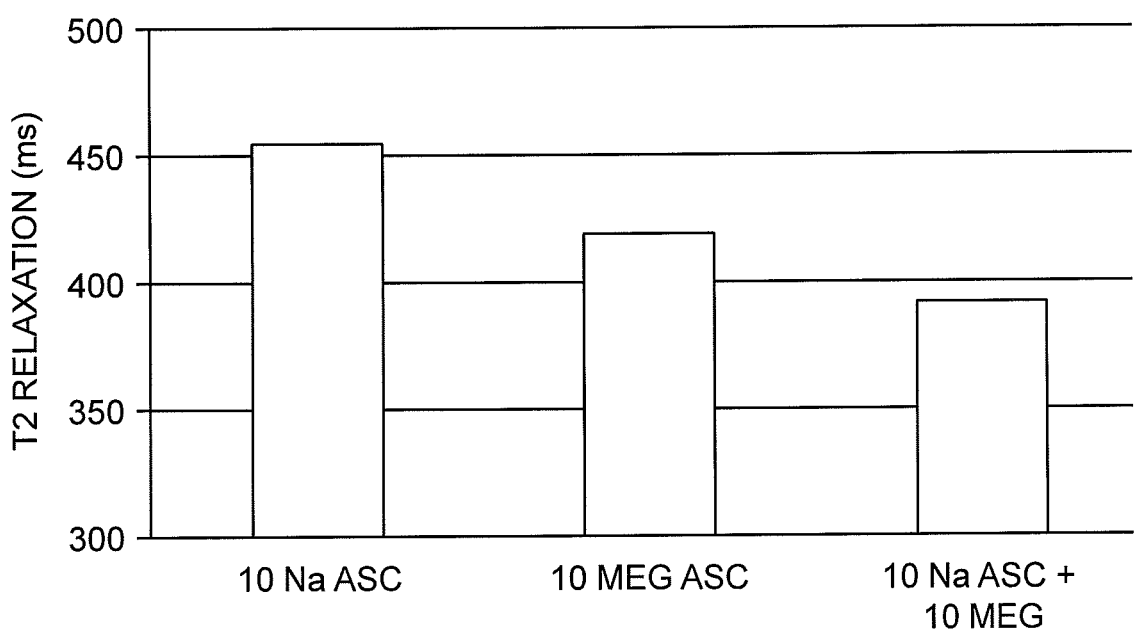
FIG. 4. Comparison of Ascorbate as Na or Meglumine Salt (Meg). Solutions are prepared with physiological concentrations of $PO_4$ (2 mM) and $HCO_3^-$ (25 mM) buffers.

It was subsequently investigated whether the impressive synergistic effect of meglumine with ascorbate was dependent on chemical association with ascorbate as a salting cation (even though in theory the two moieties should be fully dissociated in water). FIG. 4 reveals that proton exchange is actually synergized when the 'salting function' is performed by $Na^+$ cations, presumably leaving the amine group in addition to the basic OH groups of meglumine to participate in exchange catalysis with ascorbate. Note that here control $T_2$ relaxation (ms) values ($T_2$=840 ms) are not shown to better illustrate differences between experimental groups.

Figure 5:
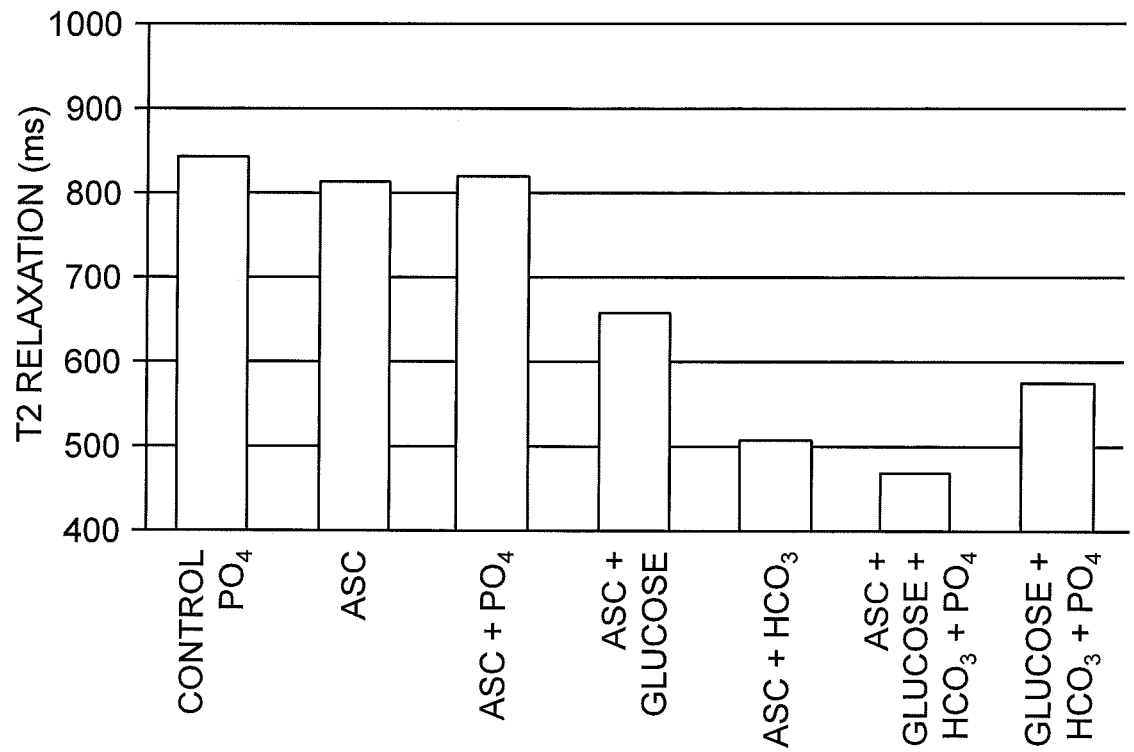
FIG. 5. Na Ascorbate (Asc)+Physiological Exchange Catalysts. Each solution is set at neutral (pH=7.0) in deionized water. Concentrations of physiological exchange catalysts are the same as the in vivo in serum and extracellular space: $PO_4$=2 mM, glucose=5 mM, and $HCO_3^-$ is 25 mM.

FIG. 5 summarizes $T_2$ relaxation data from a series of experiments looking at the influence of various physiological exchange catalysts on the contrast effect from ascorbate. Using known serum and extracellular concentrations of $PO_4$=2 mM, glucose=5 mM, and $HCO_3^-$ of 25 mM, with ascorbate at 10 mM, $T_2$ relaxation of each of these moieties was examined individually and in combination. As shown, the $T_2$ relaxation effect of ascorbate alone or with $PO_4$ in water in modest but in the presence of physiological concentrations of either glucose or $HCO_3^-$ is dramatically increased, with 10 mM ascorbate, (a concentration easily and safely achieved with parenteral administration) producing a remarkable 50% change in $T_2$ relaxation. The greatest enhancement is seen with ascorbate in the presence of glucose, $HCO_3^-$, and $PO_4$ together at known concentrations in vivo. Thus, by simply administering ascorbate i.v., the $T_2$ enhancement effect of ascorbate in vivo will be much greater than what might be expected after only looking at ascorbate alone in phantom studies without physiological exchange catalysts present.

Figure 6:
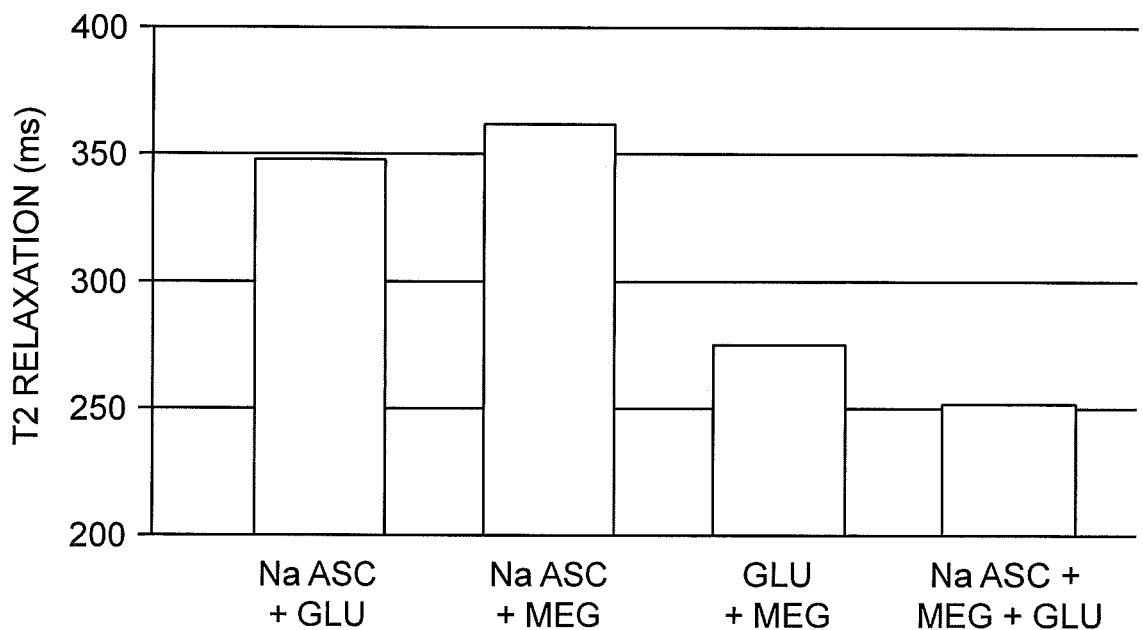
FIG. 6. Exchange Synergism Between Na Ascorbate (Na Asc)/Meglumine (Meg) and Glucose (Glu). Solutions are compared in the setting of physiological buffers $PO_4$ (2 mM) and $HCO_3^-$ (25 mM) that also contribute as exchange catalysts.

Also predicted from the experiments above is the possibility that formulation of ascorbate with other sugars that are not normally present in vivo may further catalyze the ascorbate contrast effect. FIG. 6, for example, demonstrates additional synergism when meglumine is added to a solution of sodium ascorbate at equivalent concentration (20 mM) and into a background of 2 mM $PO_4$, 25 mM $HCO_3^-$. Data show comparison with or without physiological concentrations (5 mM) of glucose, as well as the effect of meglumine alone added to the physiological catalysts. As seen the greatest contrast effect is observed when all moieties are combined. One implication therefore is that higher contrast effects may be achievable by combining different exchange catalysts with each other thus limiting the concentration of any one exogenously administered species.

Figure 7:
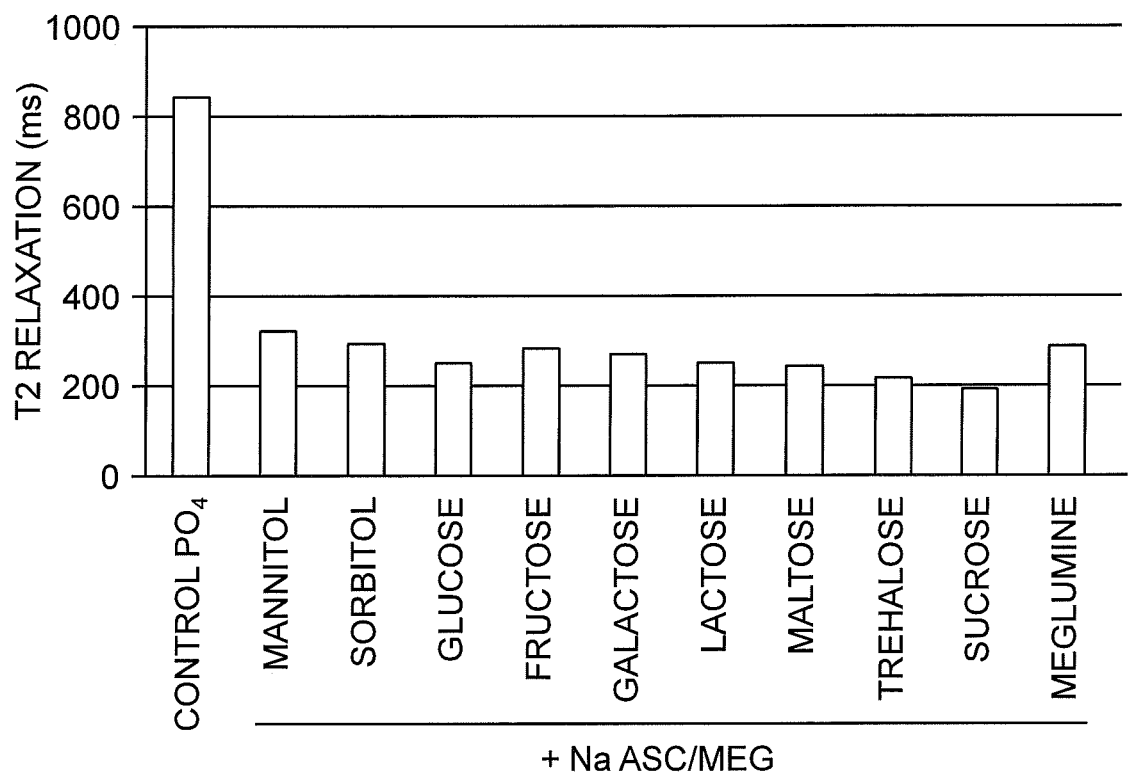
FIG. 7. Exchange synergism of Na Asc/Meglumine (Meg) with sugar alcohols, mono- and disaccharides. All solutions are prepared in co-presence of 2 mM $PO_4$ and 25 mM $HCO_3^-$.
Figure 8:
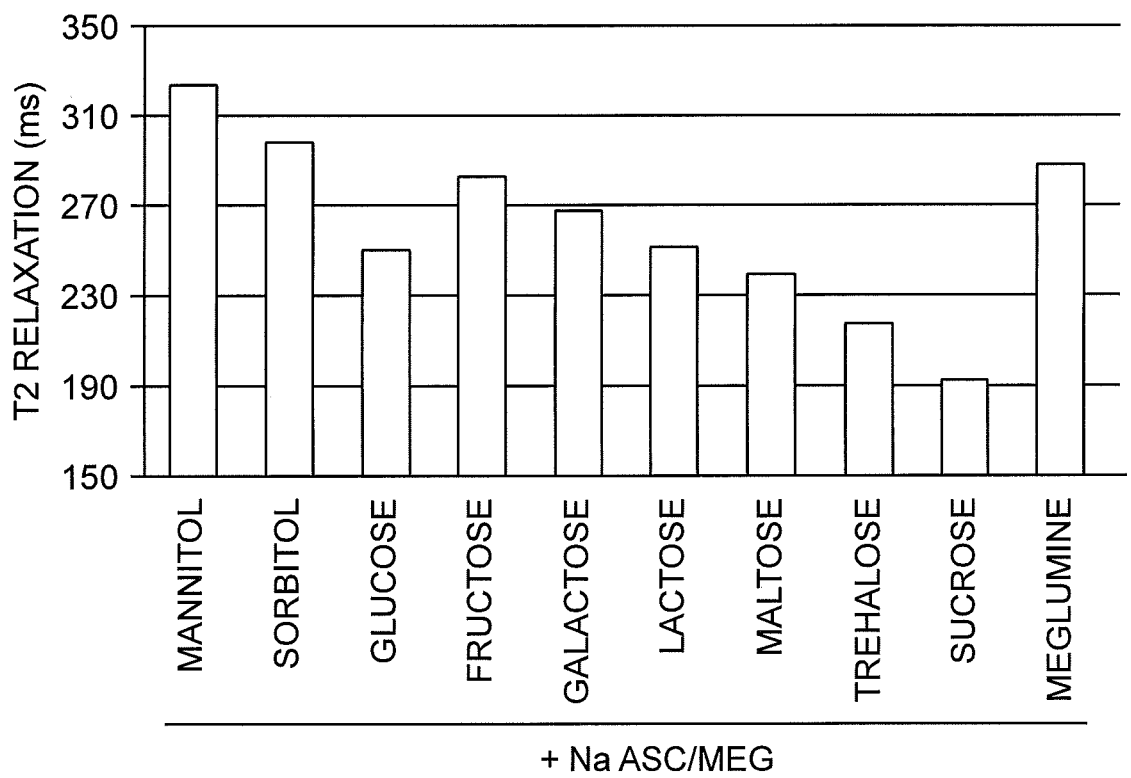
FIG. 8. Rescaled data without control for exchange synergism of Na Asc/Meglumine (Meg) with sugar alcohols, mono- and disaccharides. All solutions are prepared with 2 mM $PO_4$ and 25 mM $HCO_3^-$.

FIG. 7 summarizes data extending this concept, testing potential synergisms when Na ascorbate and meglumine are formulated with other mono and disaccharides and sugar alcohols. As shown the contrast effects are dramatic with each potential formulation. In FIG. 8, the control solution (2 mM $PO_4$ and 25 mM $HCO_3^-$) to better illustrate the differences in contrast changes between groups. The strongest effect thus observed is when ascorbate and meglumine are combined with the common disaccharide sucrose, thus suggesting a promising candidate formulation (i.e., ascorbate/meglumine/sucrose) for MRI using only moieties that may all be safely administered parenterally.

In Vivo Example 1

Normal Brain Perfusion and Metabolic Change

Figure 9A:
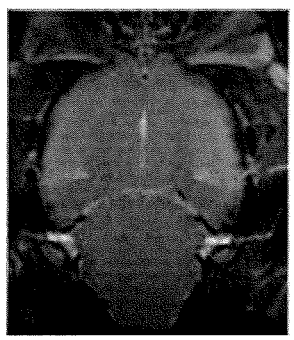
FIGS. 9A-9B. In vivo ascorbate T2 contrast changes following high dose parenteral ascorbate (2 g/kg, right IJ iv injection.)
Figure 9A:
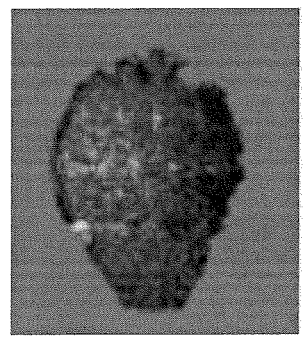
Figure 9A:
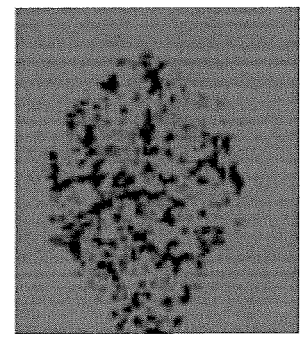
Figure 9B:
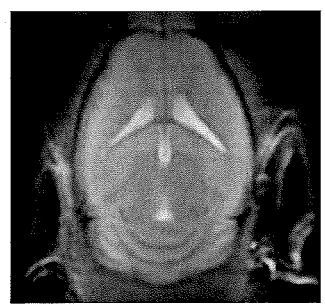
Figure 9B:
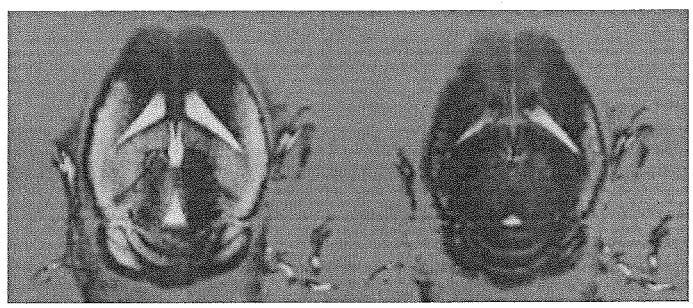
Figure 9B:

In vivo ascorbate T2 contrast changes were determined following high dose parenteral ascorbate (2 g/kg, right IJ iv injection). FIG. 9A shows a conventional single slice axial FSE T2WI image through the midbrain of a normal C57 black mouse, and the two images on the right demonstrate a 'first pass' extraction of contrast change during and following ascorbate administration i.v. T2 signal in brain tissue immediately following, and 10 minutes after, ascorbate administration is acquired and then subtracted from the T2 brain signal acquisition pre ascorbate administration. Since ascorbate produces a decrease in signal intensity, subtraction from the higher signal pre-dose scan results in a net positive 'map' of flow-through perfusion (blood flow) through brain tissue. At 10 minutes, the perfusion effect has nearly resolved and early signal intensity changes related to tissue uptake are beginning to be observed. FIG. 9B shows the signal changes due to tissue uptake of high-dose ascorbate. Color-lute maps of signal intensity are not subtracted from the pre-dose scan and therefore show the expected decreases in T2 signal over time, maximized between 30-60 min in normal C57 mice.

In Vivo Example 2

Figure 10:
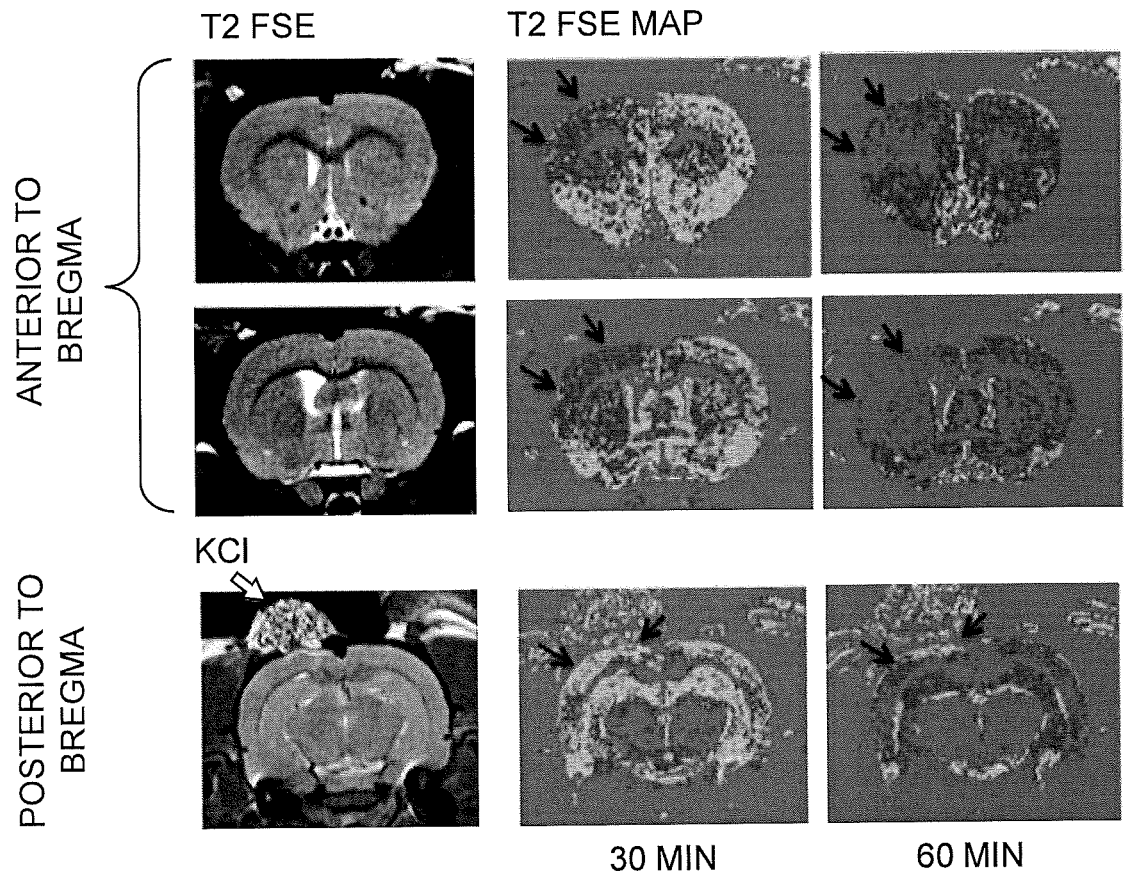
FIG. 10. Ascorbate T2 enhancement in a rodent model of neocortical spreading depression. In the illustrated experiment, the lower row of images shows a tiny craniotectomy with gelfoam (red arrow) soaked in a high concentration of KCl, which diffuses locally into the adjacent parietal cortex. The craniectomy site is 1 mm posterior to bregma, a skull landmark representing the posterior third of the underlying brain. The above two rows show T2 images and quantitative color lute T2 maps of signal change in rodent brain that are 3 and 4 mm anterior to bregma, that is, distant from the SD induction site. T2 signal changes in the anterior slices demonstrate clear T2 asymmetry in the right cerebral cortex as compared to the left (again, SD remains confined to the right hemisphere). These marked cortical signal changes are consistent with the known hypermetabolic activity that occurs with SD, as also observed with $^{18}$F-FDG PET, and with direct microdialysis and metabolomic determinations. Of note, the opposite observation (focally increased T2 signal) is seen directly under the ectom site itself (row three), consistent with localized edema (increased free water) at the site of KCl infusion.

Focal Cerebral Hypermetabolism in Association with Neocortical Spreading Depression FIG. 10 shows ascorbate T2 enhancement in a rodent model of neocortical spreading depression. Spreading depression (SD) is an experimentally reproducible pathophysiological phenomenon of CNS tissues originally described 60 years ago by Loao. After a focal region of cortex reaches a critical threshold of ionic perturbation, a massive spreading wave of cellular depolarization may begin and spread through gray matter tissue, but remain confined to the gray matter zone in which it was induced, not crossing white matter pathways. If the induction mechanism (e.g., a local high concentration of applied potassium chloride) is continuous to the same region, these waves of spreading depression will recur once every 8-10 minutes and last over a 2-3 hour period. Marked changes in brain metabolism accompany SD, and since no histologically detectable neuronal injury is present after SD, these metabolic changes parallel metabolic fluxes in non-ischemic, hyperexcitable brain tissue such as epileptogenic foci.

In the above experiment, the lower row of images shows a tiny craniotectomy with gelfoam (red arrow) soaked in a high concentration of KCl, which diffuses locally into the adjacent parietal cortex. The craniectomy site is 1 mm posterior to bregma, a skull landmark representing the posterior third of the underlying brain. The above two rows show T2 images and quantitative color lute T2 maps of signal change in rodent brain that are 3 and 4 mm anterior to bregma, that is, distant from the SD induction site. T2 signal changes in the anterior slices demonstrate clear T2 asymmetry in the right cerebral cortex as compared to the left (again, SD remains confined to the right hemisphere). These marked cortical signal changes are consistent with the known hypermetabolic activity that occurs with SD, as also observed with $^{18}$F-FDG PET, and with direct microdialysis and metabolomic determinations. Of note, the opposite observation (focally increased T2 signal) is seen directly under the craniectomy site itself (row three), consistent with localized edema (increased free water) at the site of KCl infusion.

In Vivo Example 3

Cardiac Perfusion and Metabolic Imaging

Figure 11A:
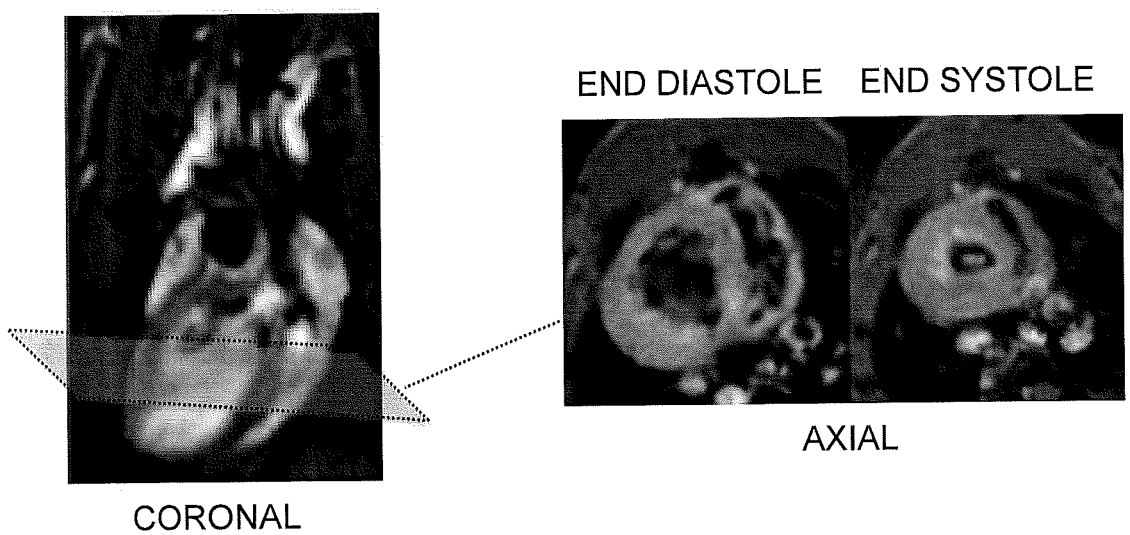
FIGS. 11A-11B. Perfusion and viability cardiac imaging with parenteral ascorbate.
Figure 11B:
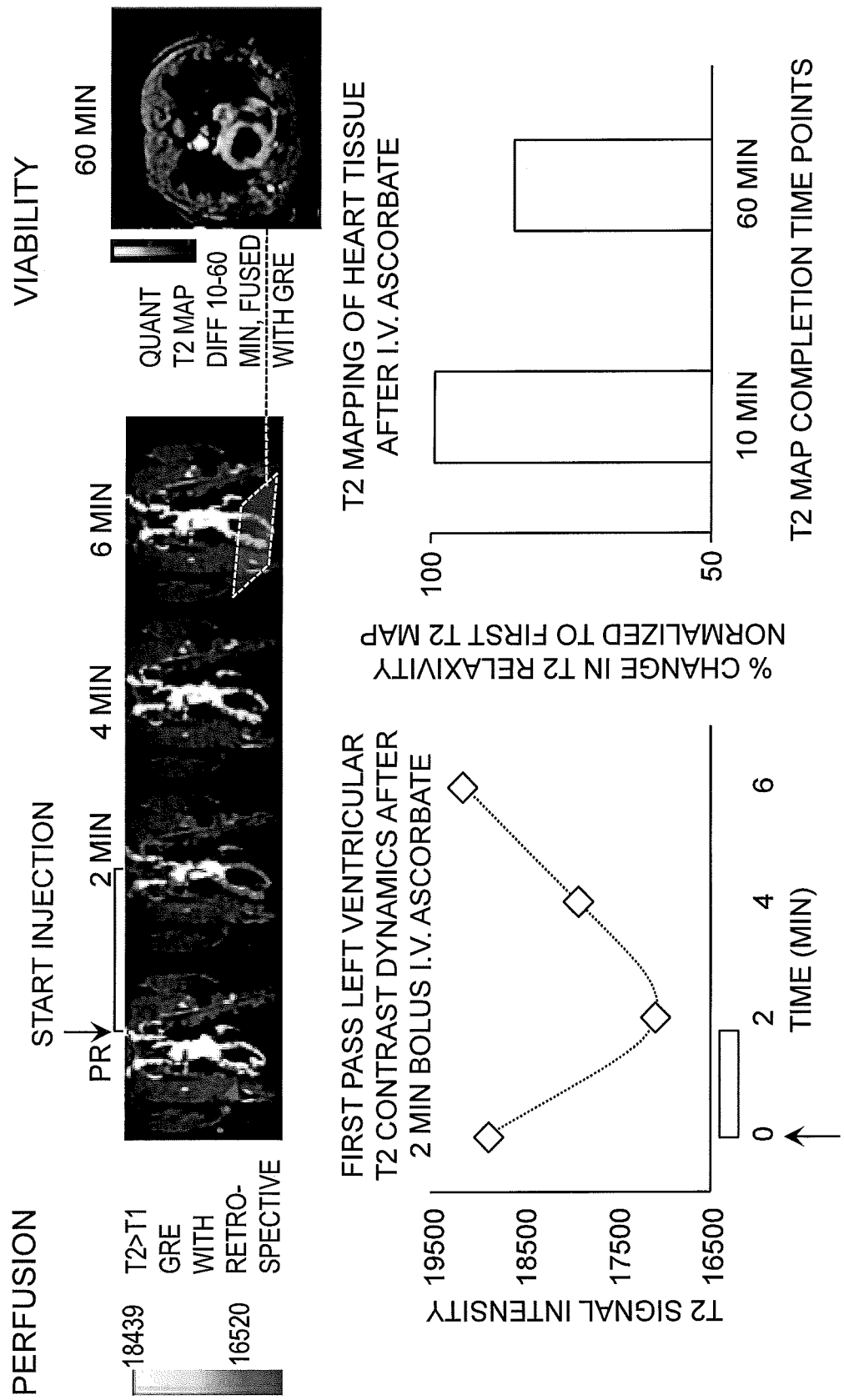

Perfusion and viability cardiac imaging with parenteral ascorbate was assessed. FIG. 11A depicts the two primary imaging planes, coronal and axial, for rat heart imaging at 7 T. Retrospective gating with respiratory coupling was employed to collect images at 7 T. The acquisition sequence is moderately T2-weighted and can be further optimized enhance the contrast effect. FIG. 11B shows transient decrease in T2 signal intensity throughout the left ventricle with initial bolus of ascorbate injection i.v. After the initial bolus for first pass flow or 'perfusion imaging' quantitative T2 maps using variable flip angles show gradual T2 contrast change in heart tissue reflecting ascorbate uptake. Only viable, metabolically active cells will take up ascorbate.

In Vivo Example 4

T2 Contrast Changes in Guinea Pigs Following Intravenous Administration of Three Different Formulations of Ascorbate We examined T2 contrast changes in whole brains of lightly anesthetized guinea pigs at 7 T. Since guinea pigs share humans' inability to synthesize ascorbate endogenously, MRI effects in this model may be more predictive of MRI changes in patients. Ascorbate was administered parenterally via femoral or jugular vein access using controlled infusion for a total dose of 2 g/kg over 60 minutes. MRI was performed for 90 minutes.

Figure 12A:
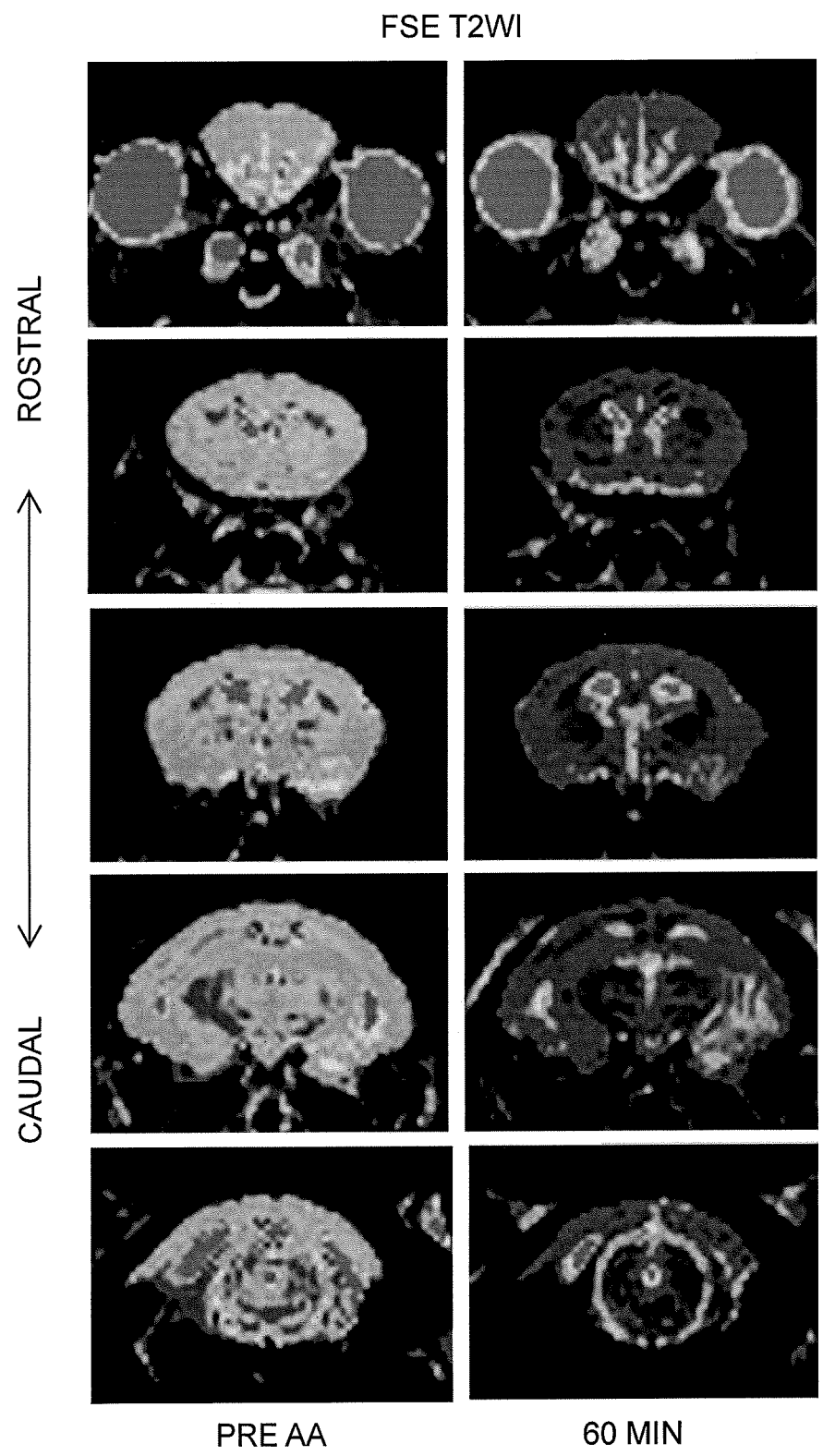
FIGS. 12A-12C. T2 contrast changes in guinea pigs following i.v. administration of three different formulations of ascorbate.

FIG. 12A shows Fast spin echo (FSE) T2 images before and after 60 min slow infusion of ascorbate show dramatic signal intensity differences throughout the brain parenchyma.

Figure 12B:
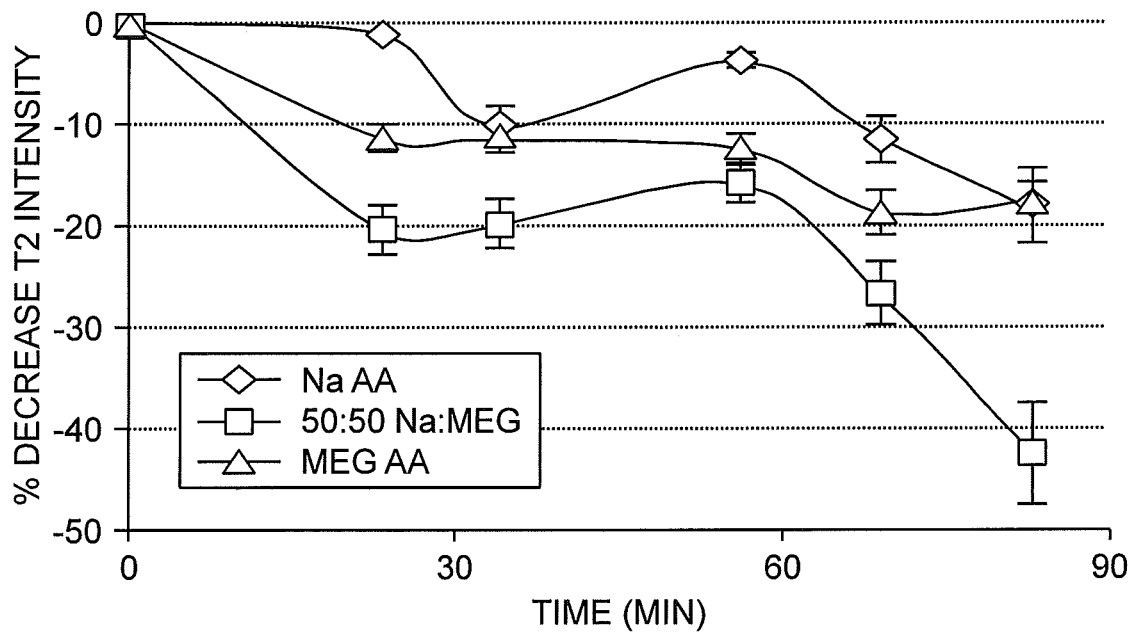
Figure 12C:
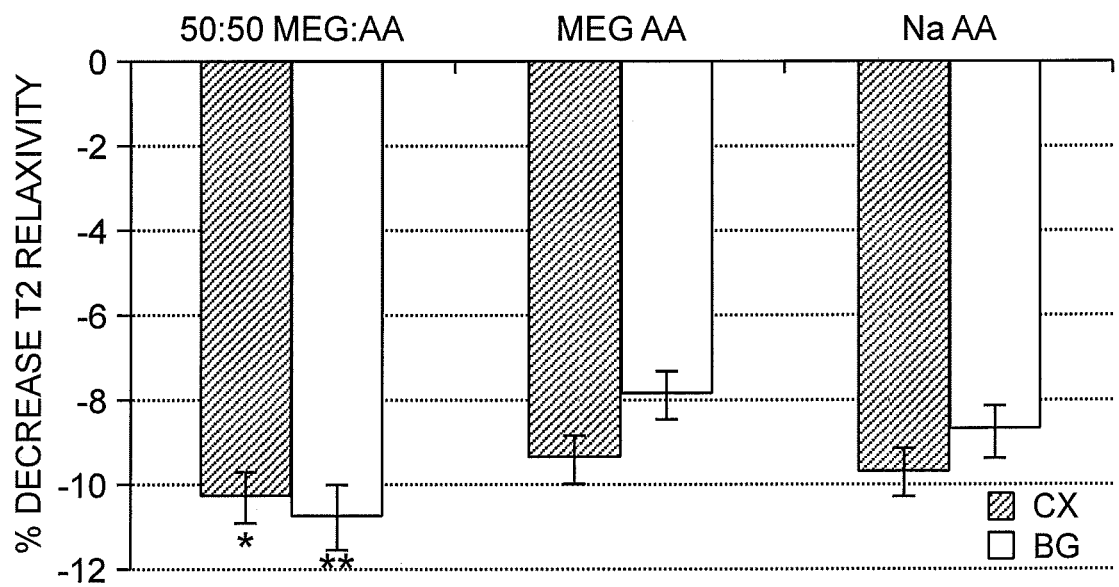

In FIG. 12B and FIG. 12C, normalized signal intensity changes and quantitative relaxivity measurements are shown for both guinea cerebral cortex (Cx) and basal ganglia (BG) after administration of three different ascorbate formulations: (1) 100% sodium ascorbate; (2) 50% sodium ascorbate and 50% meglumine ascorbate; and 3) 100% meglumine ascorbate. In FIG. 12B, signal intensity changes are greatest at each time point during and following administration of the second formulation (2) consisting of 50% Na AA: 50% Meg AA, with observed cortical FSE T2 intensity decreases exceeding 40%. Calculated T2 relaxivity values in FIG. 12C also show a greater than 10% from baseline with formulation (2), with maximal values statistically greater than either formulation (1) or (3). On conventional FSE T2 weighted images, signal intensity changes with Meg AA (3) are also noted to be greater than those observed with sodium ascorbate (1) at nearly every time point, however T2 relaxivity calculations do not show statistical differences between these latter two formulations.

The foregoing is illustrative of the present invention, and is not to be construed as limiting thereof. The invention is defined by the following claims, with equivalents of the claims to be included therein.

That which is claimed is:

1. A method of enhancing a magnetic resonance imaging (MRI) image of a body or body region, an organ or organ region in a subject, comprising:
   parenterally administering a composition comprising ascorbate or a pharmaceutically acceptable salt thereof to said subject in an MRI image-enhancing amount, wherein said composition comprises a mixture of meglumine ascorbate and sodium ascorbate provided in a molar or millimolar (mM) ratio of from 10:90 to 90:10 (meglumine ascorbate:sodium ascorbate); and then
   generating, by MRI of the subject, an image of said body or body region, an organ or organ region, whereby said composition enhances the MRI image.

2. The method of claim 1, wherein said body region is a head, neck, thorax, abdomen, pelvis, limb(s), muscle, fat, or bone.

3. The method of claim 1, wherein said organ comprises an adrenal gland, pituitary, thymus, corpus luteum, retina, brain, spleen, lung, testicle, lymph nodes, liver, thyroid, small intestinal mucosa, leukocytes, pancreas, kidney, or salivary gland tissue.

4. The method of claim 1, wherein said body region is a brain.

5. The method of claim 1, wherein said body region is a heart.

6. The method of claim 1, wherein said administering step is carried out by intravenous administration.

7. The method of claim 1, wherein said administering step is carried out by intraperitoneal administration.

8. The method of claim 1, wherein said image comprises a $T_2$ weighted image.

9. The method of claim 1, wherein said image comprises a metabolism image.

10. The method of claim 9, wherein said metabolism image is a tumor metabolism image or a brain metabolism image.

11. The method of claim 1, wherein said image comprises a perfusion image.

12. The method of claim 11, wherein said perfusion image is a cardiovascular perfusion image.

13. The method of claim 1, wherein the generating is performed during, or up to 120 minutes after, parenterally administering said composition.

14. The method of claim 1, wherein said composition further comprises a sugar or a sugar alcohol.

15. The method of claim 1, wherein said composition comprises a mixture of meglumine ascorbate and sodium ascorbate provided in a molar or millimolar (mM) ratio of from 10:90 to 60:40 (meglumine ascorbate:sodium ascorbate).

* * * * *

UNITED STATES PATENT AND TRADEMARK OFFICE
CERTIFICATE OF CORRECTION

PATENT NO. : 11,235,074 B2
APPLICATION NO. : 16/946056
DATED : February 1, 2022
INVENTOR(S) : Christopher David Lascola It is certified that error appears in the above-identified patent and that said Letters Patent is hereby corrected as shown below:

In the Specification

Column 1, Line 18: Please insert the following:
--STATEMENT OF GOVERNMENT SUPPORT
This invention was made in part with government support under grant number W81XWH-12-1-0447 awarded by the Department of Defense. The United States government has certain rights in the invention.--

Signed and Sealed this
Twenty-second Day of October, 2024

Katherine Kelly Vidal
*Director of the United States Patent and Trademark Office*